United States Patent
Higuchi et al.

(10) Patent No.: US 7,965,878 B2
(45) Date of Patent: Jun. 21, 2011

(54) ENDOSCOPIC SYSTEM WITH SPECTRAL IMAGE FORMING CIRCUIT

(75) Inventors: Mitsuru Higuchi, Saitama (JP); Shinji Takeuchi, Saitama (JP); Kazunori Abe, Saitama (JP); Daisuke Ayame, Saitama (JP)

(73) Assignee: Fujinon Corporation, Saitama-shi (JP)

(*) Notice: Subject to any disclaimer, the term of this patent is extended or adjusted under 35 U.S.C. 154(b) by 994 days.

(21) Appl. No.: 11/657,605

(22) Filed: Jan. 25, 2007

(65) Prior Publication Data

US 2007/0185378 A1  Aug. 9, 2007

(30) Foreign Application Priority Data

Jan. 27, 2006  (JP) ................ P2006-019857

(51) Int. Cl.
*G06K 9/00* (2006.01)
(52) U.S. Cl. .................................................. 382/128
(58) Field of Classification Search .......... 382/128–134; 128/920–930; 250/455–465; 356/39–49; 600/407–414, 424–426
See application file for complete search history.

(56) References Cited

U.S. PATENT DOCUMENTS

| | | |
|---|---|---|
| 4,885,634 A | 12/1989 | Yabe |
| 5,034,888 A | 7/1991 | Uehara et al. |
| 5,675,378 A | 10/1997 | Takasugi et al. |
| 5,697,885 A | 12/1997 | Konomura et al. |
| 5,717,605 A * | 2/1998 | Komiya et al. .......... 356/406 |
| 7,420,151 B2 * | 9/2008 | Fengler et al. .......... 250/208.1 |
| 2002/0175993 A1 * | 11/2002 | Ueno et al. .................. 348/68 |
| 2004/0215060 A1 | 10/2004 | Ueno et al. |

FOREIGN PATENT DOCUMENTS

| | | |
|---|---|---|
| EP | 1258221 A2 | 11/2002 |
| EP | 1488731 A1 | 12/2004 |
| EP | 1698271 A1 | 9/2006 |
| EP | 1698272 A2 | 9/2006 |
| EP | 1702556 A1 | 9/2006 |
| EP | 1702557 A2 | 9/2006 |
| JP | 2003-93336 A | 4/2003 |

OTHER PUBLICATIONS

Miyake, Yoichi, "Analysis and Evaluation of Digital Color Images," University of Tokyo Press, 2000, pp. 47, 147-153.

* cited by examiner

*Primary Examiner* — Samir A Ahmed
*Assistant Examiner* — Atiba O Fitzpatrick
(74) *Attorney, Agent, or Firm* — Birch, Stewart, Kolasch & Birch, LLP

(57) ABSTRACT

An endoscopic system that processes a color image data of a subject from an imager mounted on an endoscope and records the processed image data in an image recorder/display unit, the endoscopic system comprising: a storage that stores matrix data for forming a spectral image; and a spectral-image forming circuit that is capable of forming (i) a spectral image in an arbitrarily-selected wavelength band according to a matrix operation of the matrix data in the storage and the color image data and (ii) a standard image according to a matrix operation of standard-image matrix data and the color image data, the standard-image matrix data being for forming a standard image.

2 Claims, 5 Drawing Sheets

ENDOSCOPIC SYSTEM WITH SPECTRAL IMAGE FORMING CIRCUIT

BACKGROUND OF THE INVENTION

1. Field of the Invention

The present invention relates to endoscopic systems, and more particularly to a structure for use in a medical field and forming and displaying a spectral (video) image in an arbitrarily-selected wavelength band of image information.

2. Description of the Related Art

In the electronic endoscopes using solid-state imagers, attentions are recently drawn to the spectral imaging combined with a narrow-band pass filter depending upon the spectral reflectance upon the digestive organ (the gastric mucous membrane, etc.), i.e. narrow band imaging—NBI. The instrument is provided with three narrow-(wavelength) band-pass filters. By sequentially outputting illumination light through the narrow-band pass filters, three signals obtained from the illumination light is processed in a manner similar to those for R, G, B (RGB) signals while changing the weighting, thereby forming a spectral image. With such a spectral image, fine tissues, etc., not obtainable in the related art, can be extracted out of the digestive organ such as the large intestine.

Instead of the field-sequential type using a narrow-band pass filter, there is a proposal on forming a spectral image by an operation with an image signal obtained from white light in a simultaneous type arranging a fine-mosaic color filter for a solid-state imager, as disclosed in JP-A-2003-93336 and Yoichi Miyake "Analysis and Evaluation of Digital Color Images," University of Tokyo Press, pp 47, 147-153. This includes to determine, as matrix data (coefficient set), a relationship between a digitized data of sensitivity characteristics of RGB colors and digitized data of a spectral characteristic of through a particular narrow band, and to artificially obtain a spectral-image signal through a narrow-band pass filter by operating the matrix data with the RGB signals. Where forming a spectral image by such an operation, there is no need to prepare a plurality of filters corresponding to a desired wavelength band and hence no need to exchange those. This can avoid the instrument from increasing in size and hence lower the cost.

However, there is a tendency toward the complicated circuit configuration even for the endoscope capable of producing a spectral image based on an operation as above. There is a further need to make the structure simple. Meanwhile, devising is essentially required to efficiently obtain information useful in diagnosis, etc. through effective utilization of a plurality of spatial images different in wavelength band.

Meanwhile, in the related-art endoscope, the color image taken of a subject is recorded (filed) in the image recorder/display unit. The spectral image as above can be recorded in the image recorder/display unit in order for later observation. However, with such a spectral image, because various fine tissues can be rendered by selecting the wavelength band thereof, there are cases that the spectral images to record is in a plurality or a multiplicity in the number. In such a case, reference information is necessarily recorded at the same time. Namely, by selecting a wavelength band, various fine tissues can be rendered including, say, a comparatively thick blood vessel, a capillary vessel, a blood vessel deep in position, a blood vessel shallow in position and a cancerous tissue. Meanwhile, it is possible to render, as a target, a difference between particular substances, e.g. a difference between oxy-hemoglobin and deoxy-hemoglobin. Moreover, in order to extract a particular fine tissue successfully, there is a need of regulating a wavelength band to select. For forming and observing such a spectral image, its wavelength band constitutes vital information.

Meanwhile, the spectral image is generated based on the usual color image as an original image. When observing a spectral image, if comparison can be done with its basic color image, the subject can be easily observed/diagnosed thus obtaining an instrument easier to handle. Furthermore, where there are a plurality or multiplicity of spectral images to record, efficient recording operation, etc. are desired.

SUMMARY OF THE INVENTION

The present invention has been made in view of the foregoing problems, and it is an object thereof to provide an endoscopic system that is made simple in structure and capable of effectively making use of a plurality of spectral images different in wavelength bands wherein, upon recording a spectral image, the subject is facilitated to observe/diagnose its fine tissue while recording operation is possible to perform with efficiency.

In order to achieve the foregoing object, according to a first aspect of the invention, there is provided an endoscopic system that processes a color image data of a subject from an imager mounted on an endoscope and records the processed image data in an image recorder/display unit, the endoscopic system comprising: a storage that stores matrix data (coefficient set) for forming a spectral image; and a spectral-image forming circuit that is capable of forming (i) a spectral image in an arbitrarily-selected wavelength band according to a matrix operation of the matrix data in the storage and the color image data and (ii) a standard image according to a matrix operation of standard-image matrix data and the color image data, the standard-image matrix data being matrix data for forming the standard image.

According to a second aspect of the invention, there is provided the endoscopic system, further comprising a still-image memory that stores a still image obtained based on freeze (still image-forming) operation, the still-image memory being frontward of the spectral-image forming circuit, wherein the spectral-image forming circuit forms a spectral image depending upon a still image in the still-image memory.

According to a third aspect of the invention, there is provided the endoscopic system, further comprising a record-data output circuit that outputs the spectral image and a wavelength information about the spectral image to the image recorder/display unit.

According to the above structure, on the processor unit side, the matrix data having sixty-one wavelength-band parameters (coefficient sets p1-p61) that, say, the wavelength band of from 400 to 700 nm is segmented at an interval of 5 nm is recorded in an operation memory in order to determine signals $\lambda 1, \lambda 2, \lambda 3$ in narrow wavelength bands (components) according to a matrix operation on RGB signals. In the case to obtain a spectral image, when the operator selects three wavelength bands (satisfactorily one wavelength band) by means of wavelength selecting means, the matrix data relevant to the three wavelength bands is read out of the memory. The spectral-image forming circuit operates signals $\lambda 1, \lambda 2, \lambda 3$ from the matrix data and the DSP, etc. and forms a spectral image based on the signals $\lambda 1, \lambda 2, \lambda 3$. The spectral image can be formed plurality in different wavelength bands without limited to one in the number.

Meanwhile, in the case to generate a standard image, by providing standard-image matrix data (coefficients) in the matrix operation, the color original image itself is image-processed as a standard image. Both standard and spectral images can be generated only by the spectral-image forming circuit without switching over to the color-signal processing circuit used in the related art or the like.

Meanwhile, according to the structure of the second aspect of the invention, a plurality of spectral images in an arbitrarily-selected wavelength band can be generated by use of, as an original image, a desired or optimal-status image stored in the still-image memory by freeze operation, thus enabling to observe image information useful for diagnosis. During recording, the color image and one or a plurality of spectral images are associated together. Both are sent/recorded from the processor unit to the image recorder/display unit. The spectral images are recorded with wavelength information attached therewith.

DETAILED DESCRIPTION OF THE INVENTION

Figure 1:
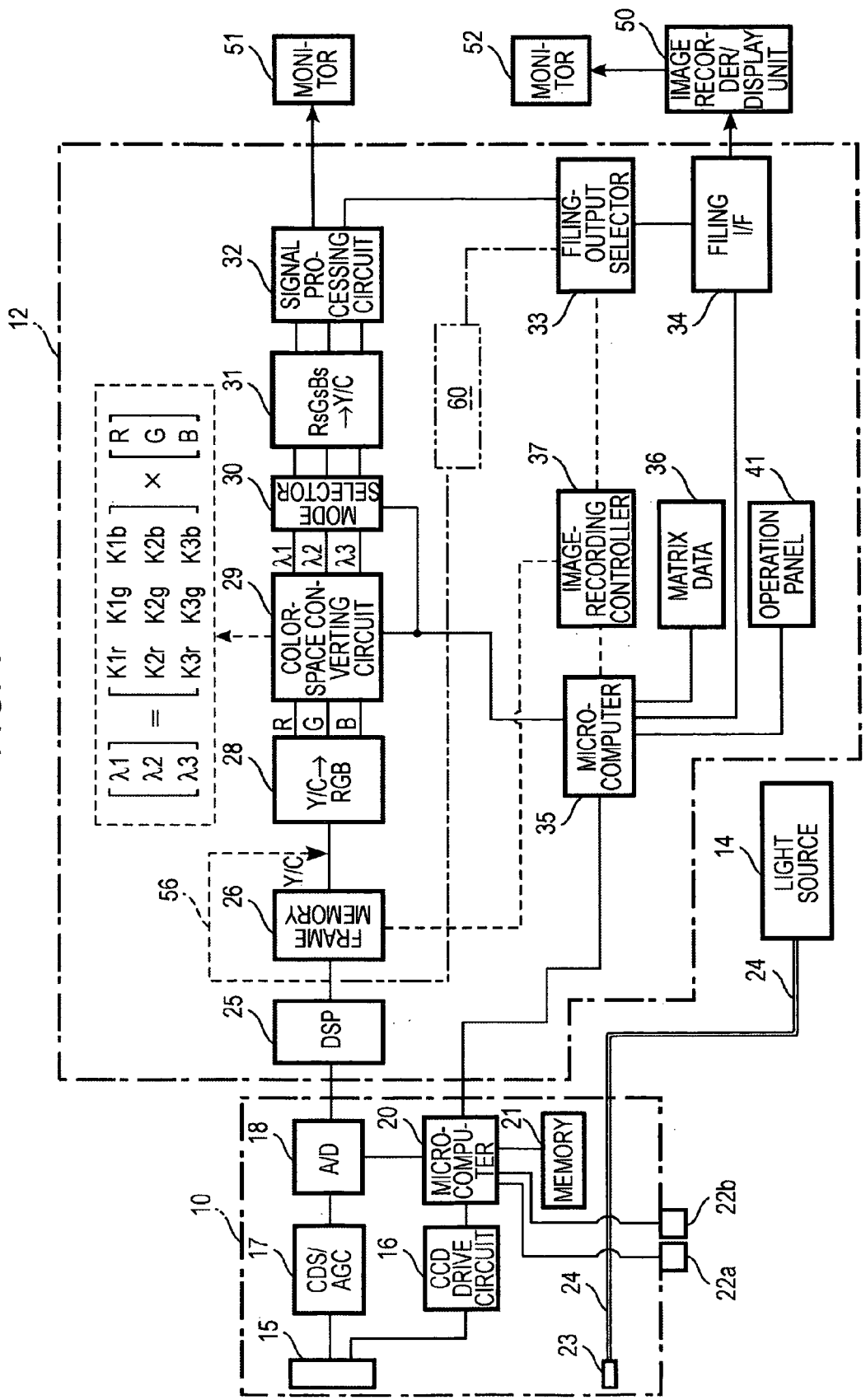
FIG. 1 is a block diagram showing an arrangement of an endoscopic system according to an embodiment of the invention.

FIG. 1 shows a configuration of an electronic endoscopic system according to an embodiment. In the electronic endoscope, a scope (electronic endoscope) 10 is provided removal from a processor unit 12 and a light source 14, as shown in the figure. The processor unit 12 is connected with an image recorder/display unit 50 and a monitor 51. The image recorder/display unit 50 is connected with another monitor 52 for use in the reproduction-display for observation/diagnosis after examined. Incidentally, the light source 14 in some cases is configured integral with the processor unit 12. The scope 10 is provided with a CCD 15, i.e. a solid-state imager, at the tip thereof. The CCD 15 uses a complementary-color type having a primary-color filter in Mg (magenta), Ye (yellow), Cy (cyan) and G (green), or a primary-color type having a color filter in R (red), G (green) and B (blue).

For the CCD 15, a CCD drive circuit 16 is provided to form a drive pulse depending upon a synchronization signal, a CDS/AGC (correlated-double sampling/auto gain control) circuit 17 to sample and amplify the image (video) signal inputted from the CCD 15, and an A/D converter 18. Meanwhile, there are arranged a microcomputer 20 to take control of various circuits of the scope 10 and of communication with the processor unit 12 (microcomputer 35), and a memory (ROM or the like) 21 to store drive information to the CCD 15, identification information about the scope 10, etc. Furthermore, the scope 10 is provided with a freeze (still image) switch 22a and a record switch 22b in an operation area thereof, and an illumination window 23 at the tip thereof. The illumination window 23 is connected to the light source 14 through a light guide 24.

Meanwhile, the processor unit 12 is provided with a DSP (digital signal processor) 25 that performs various image processes on the digitized image signal. The DSP 25 is to form and output a Y/C-signal configured by a luminance (Y) signal and a chrominance [C(R-Y, B-Y)] signal from the output signal of the CCD 15. The DSP 25 may be arranged at the scope 10 end. The DSP 25 is connected with a frame memory 26 that stores, as an original image, the 1-frame image (Y/C-signal) outputted from the DSP 25. The frame memory 26 is basically to function as a still-image memory, but is used also in forming a moving image in the embodiment. Incidentally, when forming a moving image, the signal of from the DSP 25 may be forwarded to the following stage via a through-line 56 without passing it through the frame memory 26.

For the DSP 25, a first color-conversion circuit 28 is provided so that the first color-conversion circuit 28 can convert the Y (luminance)/C (chrominance) signals, outputted from the frame memory 26, into RGB signals. In the stage following the first color-conversion circuit 28, there are provided a color-space converting circuit 29 to perform a matrix operation for a spectral image and output a spectral-image signal having a selected wavelength λ1, λ2, λ3, a mode selector 30 to select any of a spectral image having one wavelength band (narrow band) (single-color mode) and a spectral image having three wavelength bands (three-color mode) (two-color mode may be provided to select two colors, for the mode selector), a second color-conversion circuit 31 to input, as Rs, Gs, Bs signals, an image signal (λ1, λ2, λ3) having one or three wavelength bands in order to make a processing corresponding the related-art RGB signals and to convert the Rs, Gs, Bs signal into a Y/C-signal, and a signal-processing circuit 32 to perform a signal processing (mirror-image process, mask generation, character generation, etc.) other than that. A spectral-image forming circuit is provided by those of from the first color-conversion circuit 28 to the second color-conversion circuit 31. The spectral-image forming circuit generates also a standard image, as referred later. The signal processing circuit 32 outputs a signal (standard image and spectral image) that is supplied onto a monitor 51.

Meanwhile, in the FIG. 1 processor unit 12, there are provided a filing-output selector 33 to input the data of standard and spectral images outputted from the signal processing circuit 32, and a filing I/F (interface) 34 to send image data (still and moving images) to the image recorder/display unit 50. In the processor unit 12, there are further provided a microcomputer 35 to communicate with the scope 10 (microcomputer 20) and control the circuits of the device 12, to read matrix data from the memory 36 and provide it to the color-space conversion circuit 29 and to take control for freeze and record operations, and an image-recording controller 37 to control the image recording during recording.

Namely, when a freeze switch 22a of the scope 10 is operated, writing data to the frame memory 26 is prohibited so as to hold the still-image data stored in the still-image frame memory 26. Meanwhile, when recording is made by a record switch 22b, a record-control signal is supplied to the image-recording controller 37 through the microcomputers 20, 35 so that the image-recording controller 37 takes control of data output of the usual color image through the filing-output selector 33. When selected to form a spectral image, control is made to data-output the formed spectral image together with the original image through the filing-output selector 33 while storage-controlling the original image in the frame memory 26.

The memory 36 stores therein a matrix (coefficient) data (table) for forming a spectral image depending upon the RGB signals. In the embodiment, the matrix data stored in the memory 36 is exemplified in Table 1.

TABLE 1

| Parameter | $k_{pr}$ | $K_{pg}$ | $k_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −3.6E-05 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |

The matrix data in Table 1 has sixty-one wavelength-based parameters (coefficient sets) p1-p61 that, for example, a wavelength band of 400 to 700 nm is segmented at an interval of 5 nm. The parameter p1-p61 is constituted with coefficients $k_{pr}$, $k_{pg}$, $k_{pb}$ (p: corresponding top p1-p61) for matrix operation.

The color-space conversion circuit 29 performs a matrix operation according to the following equation 1, by use of the coefficients $k_{pr}$, $k_{pg}$, $k_{pb}$ and the RGB signals outputted from the first color-conversion circuit 28.

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{2b} \\ k_{3r} & k_{3g} & k_{3b} \end{bmatrix} \times \begin{bmatrix} R \\ G \\ B \end{bmatrix}$$ [Equation 1]

Namely, in the case of selecting, say, Table 1 parameters p21 (center wavelength: 500 nm), p45 (center wavelength: 620 nm) and p51 (center wavelength: 650 nm) as λ1, λ2, λ3, it is satisfactory to substitute (−0.00119, 0.002346, 0.0016) as to p21, (0.004022, 0.00068, −0.00097) as to p45 and (0.005152, −0.00192, 0.000088) as to p51 for the coefficients ($k_{pr}$, $k_{pg}$, $k_{pb}$).

Figure 2:
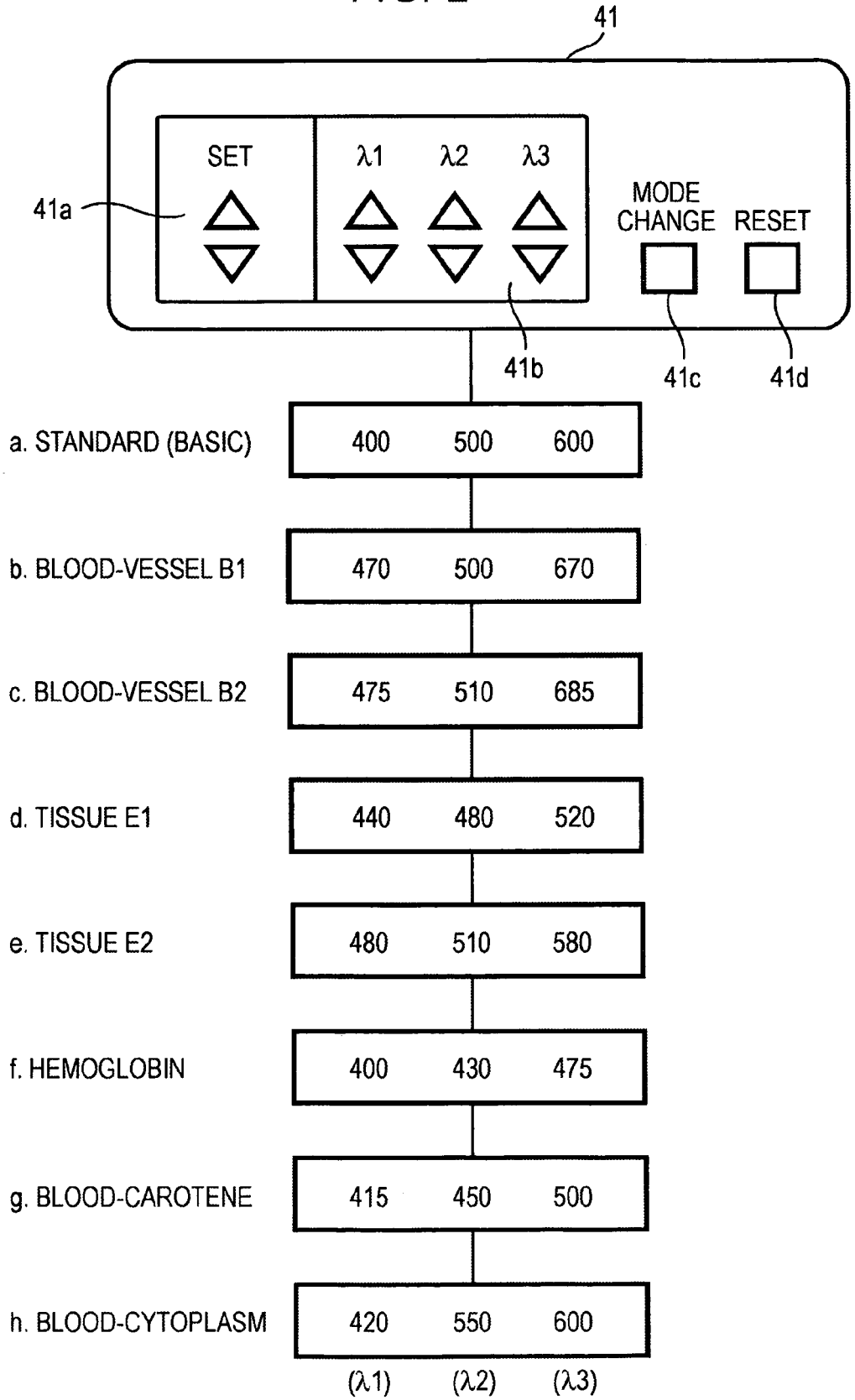
FIG. 2 is a figure showing an operation-panel arrangement of a processor unit and wavelength sets, in the embodiment.

Furthermore, the processor unit 12 has an operation panel 41 arranged thereon with operation switches for selecting a wavelength band for a spectral image, as shown in FIG. 2.

In FIG. 2, on the operation panel 41, there are arranged a set-select (changeover) switch 41a for selecting any of wavelength sets a-h, (center wavelength sets) (vertical switch for changing over the set in two directions of arrangement), a wavelength-select switch 41b for selecting respective centers of wavelength bands λ1, λ2, λ3 (vertical switch for sequentially changing over the value in two directions of increase/decrease), a mode-change switch 41c for changing between a single-color mode for a single wavelength and a three-color mode, and a reset switch 41d for returning the wavelength band to the standard value. The signals by the switches 41a-41d are supplied to the microcomputer 35.

Namely, the wavelength-select switch 41b is capable of selecting a wavelength band regardless of the bands of the wavelength sets established in the set-select switch 41a. Meanwhile, by taking the wavelength-set value selected on the set-select switch 41a as a start point, a wavelength band can be selected. The microcomputer 35 provides the color-space conversion circuit 29 with matrix data having wavelength band λ1, λ2, λ3 as selected according to the signals of from the switches 41a-41d. Incidentally, those switch functions can be assigned to the keyboard keys on the processor unit 12, etc.

In order to generate a standard image, the microcomputer 35 provides standard-image matrix data to the color-space conversion circuit 29. The standard-image matrix data has the coefficients equation 1 whose values are taken as $k_{1r}$, $k_{2g}$ and $k_{3b}$=1, $k_{2r}$, $k_{3r}$, $k_{1g}$, $k_{3g}$, $k_{1b}$ and $k_{2b}$=0. Namely, by providing coefficients to output a color original image as they are, a standard image is obtained.

The embodiment is structured as above, wherein explanation is first made on forming a standard image for a moving and still images. As shown in FIG. 1, in the scope 10, by driving the CCD 15 through the CCD drive circuit 16, the CCD 15 outputs a pickup signal of a subject-under-observation. This signal is amplified under correlated-double sampling and auto gain control in the CDS/AGC circuit 17 and then supplied as a digital signal to the DSP 25 of the processor unit 12 through the A/D converter 18. In the DSP 25, gamma processing and color-conversion processing are performed on the output signal from the scope 10, to form a Y/C-signal constituted with a luminance (Y) and chrominance (R-Y, B-Y) signals. The output of the DSP 25 is supplied to the color-space conversion circuit 29 through the first color-conversion circuit 28. In the color-space conversion circuit 29, operation processing is performed based on the standard matrix data, according to the following equation 2.

$$\begin{bmatrix} \lambda 1 \\ \lambda 2 \\ \lambda 3 \end{bmatrix} = \begin{bmatrix} 1 & 0 & 0 \\ 0 & 1 & 0 \\ 0 & 0 & 1 \end{bmatrix} \times \begin{bmatrix} R \\ G \\ B \end{bmatrix}$$ [Equation 2]

With this operation, the R, G, B signals outputted from the first color-conversion circuit 28 as they are outputted as signals λ1, λ2, λ3. By processing the signals λ1, λ2, λ3 as Rs, Gs, Bs signals in the second color-conversion circuit 31, a standard image is generated. The standard-image signal is subjected to predetermined processing such as mirror image processing, mask generation and character generation, in the following signal-processing circuit 32, and then supplied onto the monitor 51. The monitor 51 displays a color standard image in the form of the usual moving image of the subject-under-observation.

Then, when operating the freeze switch 22a, the standard image at that time is stored in the still-image frame memory 26. By prohibiting the writing of a new image signal, a still image is displayed on the monitor 51. In the embodiment, the still image can be used as an original image, namely, the person who is observing or operating is allowed to generate various spectral images in a desired or optimal state of the subject-under-observation he/she has searched/selected.

Namely, in the spectral-image forming mode of upon forming a still image, three wavelength bands are selected for the signals λ1, λ2, λ3 by operating the operation panel 41. Thereafter, when the record switch 22b of the scope 10 for example is pressed, the one-frame original image (Y/C-signal) stored in the frame memory 26 is supplied to the first color-conversion circuit 28. In this circuit 28, conversion is made from the Y/C-signal into an RGB signal. Then, the RGB signal is supplied to the color-space conversion circuit 29. In the color-space conversion circuit 29, matrix operation is performed with the RGB signal data and the matrix data, according to the foregoing equation 1 for forming, a spectral image. Namely, in forming a spectral image, the microcomputer 35 reads the matrix (coefficients) data corresponding to the three selected wavelength bands for the signals λ1, λ2, λ3 out of the memory 36 (Table 1), and supplies those to the color-space conversion circuit 29.

For example, where p21 (center wavelength: 500 nm), p45 (center wavelength: 620 nm) and p51 (center wavelength: 650 nm) are selected as three wavelength bands (λ1, λ2, λ3), signals λ1, λ2, λ3 are determined from the RGB signal by the matrix operation according to the following equation 3.

$$\begin{bmatrix} \lambda 1 \\ \lambda 2 \\ \lambda 3 \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix}$$ [Equation 3]

In the case that three-color mode is being selected by the mode-change switch 41c and mode selector 30, the signals λ1, λ2, λ3 are supplied as signals Rs(=λ1), Gs(=λ2), Bs(=λ3) to the second color-conversion circuit 31. In the case that single-color mode is being selected, any of the signals λ1, λ2, λ3 (e.g. signal λ2 when the signal λ2 is being selected) is supplied as a signal Rs, Gs, Bs to the second color-conversion circuit 31. In the second color-conversion circuit 31, the signals Rs(=λ1), Gs(=λ2), Bs(=λ3) are converted into a Y/C-signal (Y, Rs-Y, Bs-Y). The Y/C-signal is supplied onto the monitor 51 through the signal-processing circuit 32.

Figure 3:
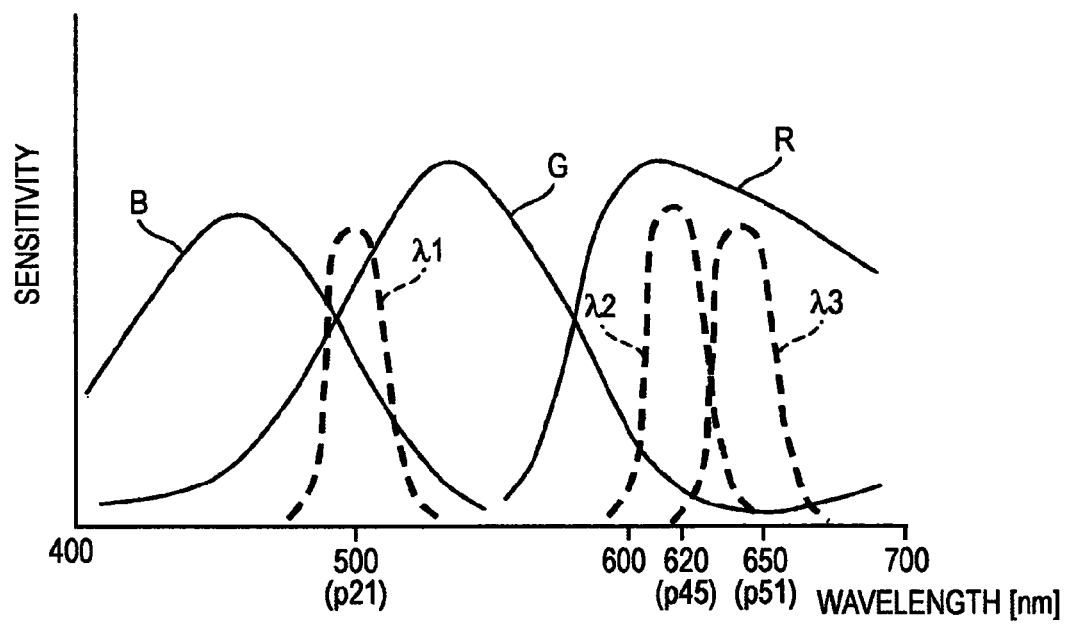
FIG. 3 is a graph showing an example of a wavelength band of a spectral image formed in the embodiment, together with a spectral-sensitivity characteristic of a primary-color type CCD.
Figure 4:
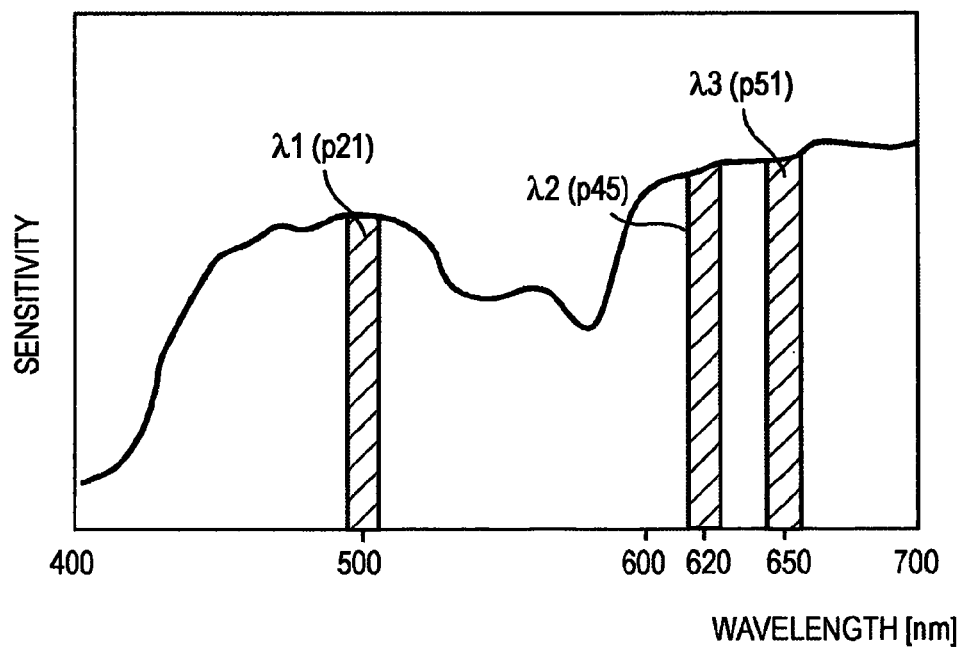
FIG. 4 is a graph showing an example of a wavelength band of a spectral image formed in the embodiment, together with a reflection spectrum from the living body.

In this manner, the spectral image displayed on the monitor 51 is constituted by the color components in wavelength bands as shown in FIGS. 3 and 4. Namely, FIG. 3 is a concept figure that the three wavelength bands forming the spectral image are superposed over the spectral-sensitivity characteristic of the color filter for the CCD 15 (primary-color type) (not necessarily matched in sensitivity scale between the color filter and the signal wavelength bands λ1, λ2, λ3). FIG. 4 is a concept figure that the three wavelength bands are superposed over the reflection spectrum from the living body. The wavelengths p21, p45, p51, selected as signals λ1, λ2, λ3 in the embodiment, are color signals respectively having center wavelengths 500 nm, 620 nm and 650 nm in order whose wavelength bands are nearly in a range of ±10 nm. A spectral image (moving and still images), constituted by a combination of such three wavelength bands of colors, is to be displayed on the monitor 51.

Now explanation is made on selecting wavelengths for the signals λ1, λ2, λ3. In the embodiment, wavelength sets are established and stored as shown in FIG. 2, e.g. (a) a standard (basic) set having 400 (center wavelength), 500 and 600 [in the order of λ1, λ2 and λ3 (nm)]; (b) a blood-vessel B1 set having 470, 500 and 670 and (c) a blood-vessel B2 set having 475, 510 and 685 that are for rendering a blood vessel (d) a tissue set E1 having 440, 480 and 520 and (e) a tissue set E2 having 480, 510 and 580 that are for rendering; a particular tissue; (f) a hemoglobin set having 400, 430 and 475 for rendering a difference between oxy-hemoglobin and deoxy-hemoglobin, (g) a blood-carotene set having 415, 450 and 500 for rendering a difference between blood and carotene, and (h) a blood-cytoplasm set having 420, 550 and 600 for rendering a difference between blood and cytoplasm. From among those, a desired wavelength set can be selected by use of the selector switch 41a. Due to this, by previously establishing a wavelength set for frequent use, it is easy to select a wavelength set.

Meanwhile, in the case the operator is to select a desired wavelength band, selecting the standard set "a" or pressing the reset switch 41d, for example, causes the monitor 51 to display 400, 500 and 600 (nm) thereon. Here, the operator is allowed to set the wavelength bands λ1, λ2, λ3 at respective desired values by operating the wavelength-select switch 41b. Furthermore, the FIG. 2 mode-change switch 41c is for changing over between single-color mode and three-color mode. In the single-color mode, the wavelength bands λ1, λ2, λ3 are all set at the same value, e.g. 470.

Figure 5:
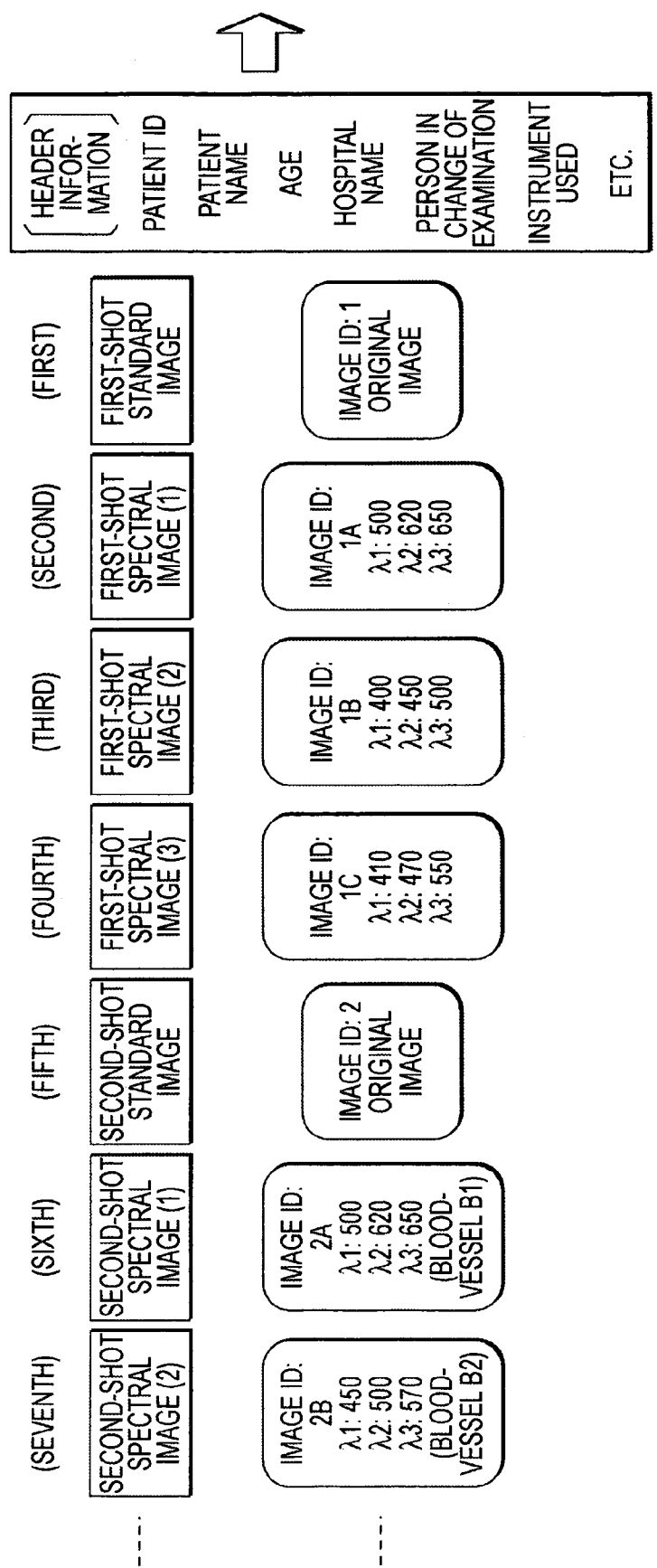
FIG. 5 is a figure showing a data content to be sent from the processor unit to the image recorder/display unit, in the embodiment.

With reference to FIGS. 5 and 6, explanation is now made on recording a spectral image (still image) to the image recorder/display unit 50. Recording a spectral image can be performed one sheet a time while setting up a desired wavelength band. However, a predetermined number, e.g. three, of spectral images can be taken as one set to previously set up the wavelength bands thereof so that four images including the original image can be processed by once operating the record switch 22 arranged in the operation area of the scope 10. In the communication of from the processor unit 12 to the image recorder/display unit 50, the spectral images are placed in association with the original image. To those images are added identification (ID) information including shot number, spectral-image process number and wavelength established.

For example, as shown in FIG. 5, when communicating a spectral image at from the processor unit 12, first outputted are information about patient ID, patient name, age, hospital name, person in charge of examination, apparatus in use, etc. (patient information, hospital information, examination information, etc.), as header information. Thereafter, through the filing-output selector 33 and filing IF 34, sent to the image recorder/display unit 50 are a first shot of image data, e.g. original-image data having an image ID of 1, spectral-image data (No. 1) added with an image ID of 1A and respective wavelength information (λ1: 500, λ2: 620, λ3: 650), spectral-image data (No. 2) added with an image ID of 1B and respective wavelength information (λ1: 400, λ2: 450, λ3: 500), spectral-image data (No. 3) added with an image ID of 1C and respective wavelength information (λ1: 410, λ2: 470, λ3: 550); and subsequently a second shot of image data having an image ID of 2; followed by spectral image data (e.g. packet) added with image IDs of 2A, 2B and 2C and respective wavelength information of λ1, λ2, λ3.

The first shot of image data is arbitrarily set with its wavelength bands. The second shot of image data is selected with the blood-vessel B1 set (b) (as the first), the tissue E2 set (e) (as the second), and the hemoglobin set (f) (as the third), that are the wavelength sets explained as wavelength bands in FIG. 2. The image data on the shots is to be communicated by once operation of the record switch 22 of the scope 10. Namely, after selecting wavelength bands for three spectral images arbitrarily or based on the wavelength sets, once operating the record switch 22 generates four, original and spectral images as an image set that are to be sent to the image recorder/display unit 50. This can generate and record a spectral image with efficiency.

Figure 6A:
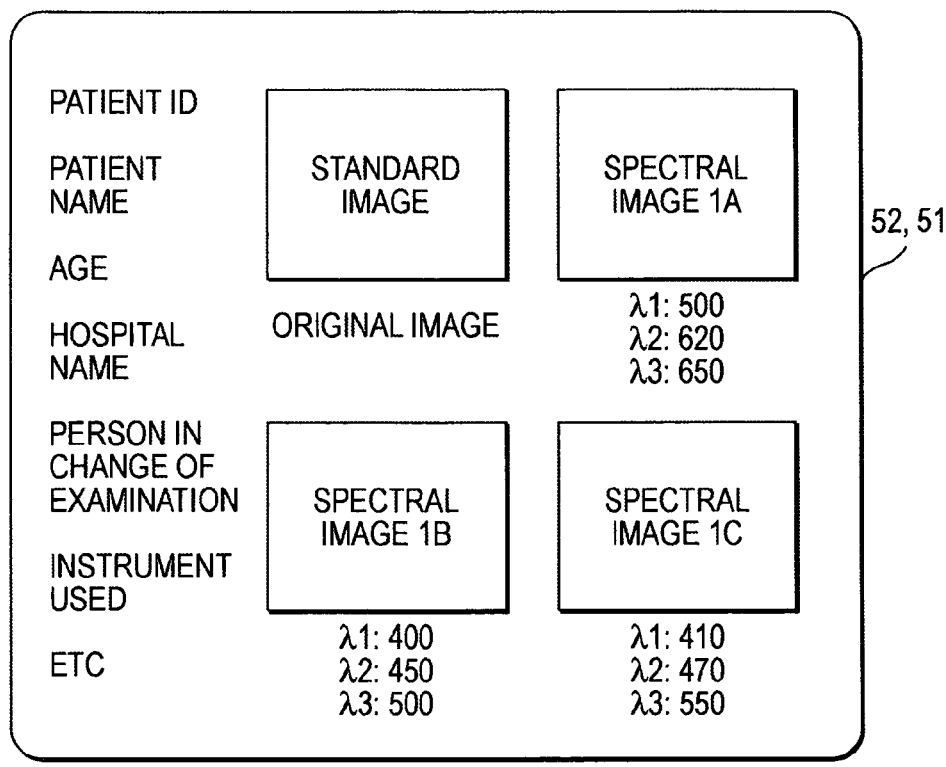
FIGS. 6A and 6B are figures showing display states of original and spectral images displayed on the monitor, in the embodiment.
Figure 6B:
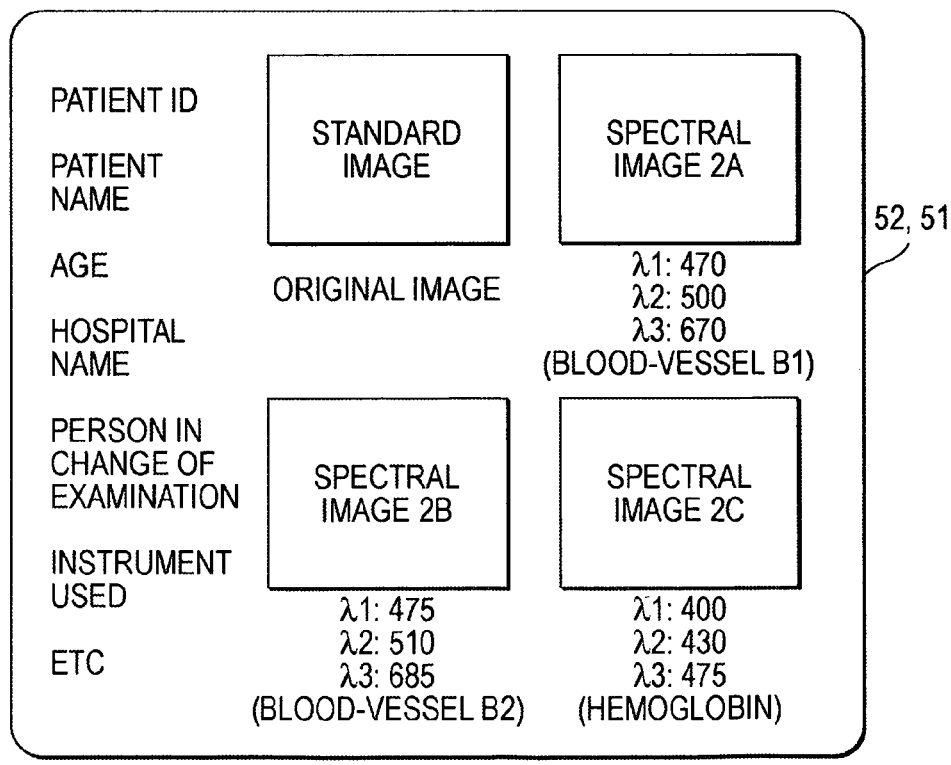

FIG. 6 shows a display state on the monitor 52 connected to the image recorder/display unit 50. In the reproduction for post-examination observation, diagnosis or the like, the four, original (standard) and spectral images in the first shot as shown in FIG. 6(A) and the four, original and spectral images in the second shot as shown in FIG. 6(B) are each displayed, in order, at small screens over one screen. On the screen, displayed are various information, including patient information. Furthermore, in the beneath, etc. of the spectral image; displayed are wavelength information ($\lambda 1, \lambda 2, \lambda 3$) making up the spectral image and a set name, etc. where a wavelength set is applied. Accordingly, for the spectral image, a target in a fine texture can be grasped swiftly and positively by means of the wavelength information and set name.

The monitor 52 in the embodiment is allowed to display one original or spectral image over the entire screen thereof. Namely, in the communication of original and spectral images as described, the image data formed by the processor unit 12 is sent as it is without decreasing the amount of data adapted for small-sized screens (divisional screens), in a manner not causing a quality deterioration when displayed over the entire screen. Furthermore, in the embodiment, the spectral image, formed during use of the scope 10, can be outputted onto the monitor 51 under control of the processor unit 12, so that a plurality of images can be displayed on one screen as shown in FIG. 6 or one image be displayed over the entire screen.

Although the operation in the above was explained on the still-image case, a moving image of spectral image can be recorded. In such a case, wavelength information can be data-communicated together with the spectral moving image to the image recorder/display unit 50 where the wavelength information can be displayed on the spectral image or the like.

As described so far, the embodiment can simplify the circuit configuration of the processor unit by use of standard-image matrix data in a matrix operation by the spectral-image forming circuit. For example, in order to additionally realize the invention, a color-signal processing circuit 60 for obtaining a standard image equivalently to the related-art circuit is provided in a form parallel with the spectral-image forming circuit at between the DSP 25 and the filing-output selector 33 or monitor 51, as shown in FIG. 1. However, the embodiment does not require such a standard-image color-signal processing circuit 60, a switch circuit for changing over between standard and spectral images, and so on.

According to the endoscopic system of the invention, both standard and spectral images are formed by only the spectral-image forming circuit, thus eliminating the need of a signal processing circuit for forming only a standard image and hence simplifying the circuit configuration for the instrument. Meanwhile, because the still-image memory is arranged in the front stage to the spectral-image forming circuit, a plurality of spectral images different in wavelength band are effectively formed and observed based upon on a desired or optimal still image searched/selected by freeze operation, thus enabling to efficiently acquire the information useful for diagnosis or the like.

Meanwhile, in recording the spectral image, the wavelength information thereof is appended. Accordingly, it is easy to observe/diagnose a fine tissue of a subject-under-observation, thus obtaining the information useful in forming a spectral image in the next time.

The entire disclosure of each and every foreign patent application from which the benefit of foreign priority has been claimed in the present application is incorporated herein by reference, as if fully set forth.

What is claimed is:

1. An endoscopic system that processes a color image data of a subject from an imager mounted on an endoscope and records the processed image data in an image recorder/display unit, the endoscopic system comprising:

a storage that stores matrix data for forming a spectral image;

a still-image memory that stores a still image obtained based on freeze operation on the color image data, the still-image memory being frontward of the spectral-image forming circuit, and a spectral-image forming circuit that forms (i) a spectral image in a selected wavelength band according to a matrix operation of the matrix data in the storage and the still image wherein an operator selects a desired wavelength band thereby extracting a particular tissue type of interest and (ii) a standard image according to a matrix operation of standard-image matrix data and the still image, the standard-image matrix data being matrix data for forming the standard image, wherein the standard image matrix data satisfies the equation

[lamda__1; lamda__2; and lamda__3]=[100; 010; 001]×[R; G; B]

where lamda__1, lamda__2, and lamda__3 represent standard image signal and R, G, and B represent the color image data.

2. The endoscopic system according to claim 1, further comprising a record-data output circuit that outputs the spectral image and a wavelength information about the spectral image to the image recorder/display unit.

* * * * *